United States Patent
Kim et al.

(10) Patent No.: US 10,493,133 B2
(45) Date of Patent: Dec. 3, 2019

(54) METHOD FOR PREPARING HIGHLY CONCENTRATED FIBRINOGEN SOLUTION AND METHOD FOR PREPARING FIBRIN SEALANT BY USING THEREOF

(71) Applicant: GREEN CROSS CORPORATION, Yongin-si, Gyeonggi-do (KR)

(72) Inventors: Jun Sic Kim, Yongin-si (KR); Gun Sul Lee, Yongin-si (KR); Ki-Yong Kim, Yongin-si (KR); Yong Kang, Yongin-si (KR); Ki Hwan Son, Yongin-si (KR)

(73) Assignee: GREEN CROSS HOLDINGS CORPORATION, Yongin-si (KR)

( * ) Notice: Subject to any disclaimer, the term of this patent is extended or adjusted under 35 U.S.C. 154(b) by 0 days.

(21) Appl. No.: 14/351,902

(22) PCT Filed: Oct. 24, 2012

(86) PCT No.: PCT/KR2012/008755
§ 371 (c)(1),
(2) Date: Apr. 15, 2014

(87) PCT Pub. No.: WO2013/062305
PCT Pub. Date: May 2, 2013

(65) Prior Publication Data
US 2014/0328822 A1 Nov. 6, 2014

(30) Foreign Application Priority Data
Oct. 27, 2011 (KR) .................. 10 2011 0110526

(51) Int. Cl.
*A61K 38/36* (2006.01)
*C07K 14/75* (2006.01)
*A61L 24/10* (2006.01)
*A61K 38/45* (2006.01)

(52) U.S. Cl.
CPC ............ *A61K 38/363* (2013.01); *A61K 38/45* (2013.01); *A61L 24/106* (2013.01); *C07K 14/75* (2013.01)

(58) Field of Classification Search
CPC ..... A61K 38/363; A61K 38/45; A61L 24/106; C07K 14/75
USPC ........................................ 424/94.5
See application file for complete search history.

(56) References Cited

U.S. PATENT DOCUMENTS

| 5,962,405 A * | 10/1999 | Seelich | A61L 24/106 514/13.6 |
| 7,241,603 B2 * | 7/2007 | Seelich | A61L 24/106 435/183 |
| 2003/0133928 A1 * | 7/2003 | Metzner | A61L 31/046 424/94.64 |
| 2005/0080009 A1 | 4/2005 | Metzner et al. | |
| 2006/0128016 A1 * | 6/2006 | Tokushima | A61L 27/225 435/404 |
| 2010/0119563 A1 * | 5/2010 | Miyagawa | A61K 38/363 424/402 |

FOREIGN PATENT DOCUMENTS

| WO | 01/12244 A1 | 2/2001 |
| WO | 03/028654 A2 | 4/2003 |
| WO | 03/028743 A1 | 4/2003 |
| WO | 03/047530 A2 | 6/2003 |
| WO | 2011104381 A2 | 9/2011 |

OTHER PUBLICATIONS

PubChem CID 23672308: Sodium Glutamate. Create date: Feb. 5, 2008. (Year: 2008).*
PubChem CID 66250: L-Arginine Hydrochloride. Create date: Jun. 24, 2005. (Year: 2005).*
International Searching Authority International Search Report for PCT/KR2012/008755 dated Mar. 29, 2013.

* cited by examiner

Primary Examiner — Sean C. Barron
(74) Attorney, Agent, or Firm — Sughrue Mion, PLLC

(57) ABSTRACT

A method for preparing a highly concentrated fibrinogen solution includes adding amino acid or amino acid derivatives, and/or salts to a lowly concentrated fibrinogen solution, followed by a ultra-filtration concentration. Factor XIII can be added either before or after the ultra-filtration to give a fibrin sealant component 1 containing the highly concentrated fibrinogen solution. The fibrin sealant component 1 could be preserved for a long time at room temperature and be used without a reconstitution. Fibrin sealant component 2 is a solution containing thrombin and calcium. A fibrin sealant product may be provided in a vial type in which the fibrin sealant components 1 and 2 are each filled in separate vials or in a re-filled syringe type wherein the fibrin sealant components 1 and 2 are each filled in separate syringes connected with each other to be instantly used.

8 Claims, 3 Drawing Sheets

METHOD FOR PREPARING HIGHLY
CONCENTRATED FIBRINOGEN SOLUTION
AND METHOD FOR PREPARING FIBRIN
SEALANT BY USING THEREOF

CROSS REFERENCE TO RELATED
APPLICATIONS

This application is a National Stage of International Application No. PCT/KR2012/008755 filed Oct. 24, 2012, claiming priority based on Korean Patent Application No. 10-2011-0110526 filed Oct. 27, 2011, the contents of all of which are incorporated herein by reference in their entirety.

TECHNICAL FIELD

The present invention relates to a method for preparing a highly concentrated fibrinogen solution and a method for preparing a fibrin sealant component 1 containing the highly concentrated fibrinogen solution and Factor XIII. More specifically, the method for preparing a highly concentrated fibrinogen solution according to the present invention is characterized by adding amino acid or amino acid derivatives, salts, and/or the like, to a lowly concentrated fibrinogen solution separated from blood plasma and then preparing highly concentrated fibrinogen therefrom using an ultra filtration method. The method for preparing a fibrin sealant component 1 in order to be used in a fibrin sealant product is characterized by adding Factor XIII before or after the ultra filtration in the method of preparing a highly concentrated fibrinogen solution. Here, a fibrin sealant component 1 according to the present invention is preferably a solution state.

The fibrin sealant component 1 prepared by the method according to the present invention may be frozen in a liquid state, be preserved for a long time storage at room temperature, and be immediately applied to treatment without performing a reconstitution process.

In addition, the present invention relates to a fibrin sealant product configured of the fibrin sealant component and a fibrin sealant component 2, which is a solution containing thrombin and calcium chloride filled in a separate container. The fibrin sealant product according to the present invention may be provided in a vial type in which the fibrin sealant component 1 and the fibrin sealant component 2 are filled in separate vials, respectively, or a pre-filled type in which the fibrin sealant component 1 and the fibrin sealant component 2 are filled in separate syringes connected with each other to thereby be immediately used.

BACKGROUND ART

A fibrin sealant, which is called a fibrin glue or a fibrin tissue adhesive, uses a human body blood clotting mechanism. More specifically, blood clotting is made through chain reactions of blood clotting factors, and fibrinogen, Factor XIII, and thrombin, or the like, are involved in a final step of the clotting pathway. Here, the fibrin sealant use the principle that Factor XIII, fibrinogen, calcium chloride, and thrombin are mixed to form a fibrin polymer, and at this time, Factor XIII serves to crosslink the fibrin polymers, such that the fibrin polymer is converted into insoluble fibrin polymer.

The fibrin sealant applies the blood clotting mechanism described above to an adhesive. That is, the fibrin sealant is based on the principle that when a wound, or the like, occurs in tissue, fibrinogen is released together with blood components from capillary blood vessels around the wounded tissue to form fibrin, thereby adhering to the surroundings of the wound. Applications of the fibrin sealant for treatment purpose such as adhesion to tissue and hemostasis, playing a supportive role for healing a wound, or the like, have been continuously widened. The fibrin sealant has biological advantages such as not having coagulation disorder with platelets, excellent histocompatibility, and appropriate absorption, or the like, in addition to physical advantages such as rapid adhesion, not being affected by moisture of an adhering portion, or the like, such that the fibrin sealant has been significantly spotlighted as the next-generation medical adhesive.

Clinical studies of the fibrin sealant on a suture of a peripheral nerve, a suture of micro-vessel using tissue adhesion action of the fibrin sealant based on the advantages of the fibrin sealant as described above has been conducted in Europe, and the fibrin sealant has been used in vascular surgery, surgery, neurosurgical operation, adhesion of bone, or the like, as an adhesive for surgery in Japan.

In order to prepare this fibrin sealant, initially, thrombin, which is one of the fibrin components, was separated from bovine blood plasma to be used (Patent Document 1, U.S. Registration Pat. No. 4,627,879) in Europe, but was not sold due to a safety problem, or the like, outside of Europe. In addition, although fibrin sealant formulations using autologous blood (See U.S. Pat. Nos. 4,714,457, 5,030,215, or the like) has been developed, since a blood sampling process and additional manufacturing processes were required, it was significantly inconvenient to be clinically used.

Therefore, in the fibrin sealant prepared from human blood plasma to be commercially sold, safety against a virus should be secured and the clinical use should be convenient.

Recently, as the fibrin sealant, a freeze-dried type fibrin sealant and a frozen-liquid type fibrin sealant have been marketed. In the freeze-dried type fibrin sealant, since a dissolution time of fibrinogen was long and it took a relatively long time to be reconstituted, it was inconvenient in that the freeze-dried fibrin sealant should be rapidly used. On the other hand, the frozen-liquid product has an advantage in that it takes a relatively short time to be actually used as compared to the freeze-dried type product. A representative product is Tisseel (Baxter Healthcare Corp.). Tisseel is being sold as a pre-filled type product that may be frozen in a liquid state, that is, a ready-to-injection form product that may be immediately injected, and estimated as a product significantly reducing a preparation time for use.

However, in the case of the frozen-liquid product, there are disadvantages that solvent/detergent (S/D) treatment and heat treatment using steam should be performed in order to remove any virus derived from the blood (See U.S. Pat. No. 5,962,405 and Tisseel data (www.baxter.com)).

Particularly, there was inconvenience in that freeze-drying should be performed in the middle of the process in order to perform the thermal-treatment using steam (See European Patent Publication No. 345246 and European Patent Publication No. 159311). In addition, since a method of freeze-drying fibrinogen to dissolve fibrinogen is used in order to obtain highly concentrated fibrinogen, there is inconvenience in that the freeze-drying process should be performed in order to obtain fibrinogen solution having a high concentration, particularly, a concentration of 70 mg/mL or more that is required to prepare the fibrin sealant.

A technology capable of solving the problem in the process of preparing the fibrin sealant currently used as described above and more economically and easily preparing the fibrin sealant, particularly, a technology capable of more economically, easily, and highly concentrating fibrinogen to prepare the fibrin sealant has been urgently required.

RELATED ART DOCUMENT

Patent Document (Patent Document 1) U.S. Pat. No. 4,627,879: Fibrin adhesive prepared as a concentrate from single donor fresh frozen plasma, Granted: Dec. 9, 1986, Patentee: Rose et al.

(Patent Document 2) U.S. Pat. No. 4,714,457: Method and apparatus for use in preparation of fibrinogen from a patients blood, Granted: Dec. 22, 1987, Patentee: Alterbaum.

(Patent Document 3) U.S. Pat. No. 5,030,215: Preparation of fibrinogen/Factor XIII precipitate, Granted: Jul. 9, 1991, Patentee: Morse et al.

(Patent Document 4) U.S. Pat. No. 5,962,405: Storage-stable fibrinogen preparations, Granted: Oct. 5, 1999, Patentee: Seelich.

DISCLOSURE

Technical Problem

In order to solve these problems, the present inventors conducted continuous studies, and developed a method for preparing a highly concentrated fibrinogen solution and a fibrin sealant component 1 capable of securing safety against a virus derived from human blood plasma and being used to prepare the fibrin sealant product that may be preserved at room temperature and frozen in a liquid state, without a freeze-drying process, thereby completing the present invention.

Technical Solution

In one general aspect, there is provided a method for preparing a highly concentrated fibrinogen by adding amino acid or amino acid derivatives, and/or salts, etc. to a lowly concentrated fibrinogen solution and concentrating the fibrinogen solution through an ultra filtration process, and additionally, a method for preparing a fibrin sealant component 1 further including adding Factor XIII in addition to the above mentioned method, and a method for the preparing fibrin sealant.

Hereinafter, the present invention will be described in detail.

Although it was known in the art that it is impossible to highly concentrate fibrinogen using the ultra filtration due to high viscosity of the fibrinogen solution, the present inventors discovered that in the case in which amino acid or the amino acid derivative, and/or salts, etc. are added to the solution containing fibrinogen, the viscosity of the solution is significantly reduced, such that the ultra filtration may be easily applied. That is, in the method for preparing a highly concentrated fibrinogen solution according to the present invention, amino acid or the amino acid derivative, and/or salts, etc. are added to the lowly concentrated fibrinogen solution obtained from the blood plasma, and then ultra filtration process is performed.

In the present invention, the term "lowly concentrated fibrinogen solution", which is a solution obtained by separating materials cryoprecipitated from the human blood plasma using cryoprecipitation method and by performing generally known processes such as virus inactivation method using solvent/detergent, or the like, anion chromatography, glycine precipitation method, or the like, means a solution that is not concentrated through the ultra filtration process. A content of fibrin in the lowly concentrated fibrinogen solution may be smaller than 40 mg/mL, and preferably, be 35 mg/mL or less.

For example, the lowly concentrated fibrinogen solution may be obtained in high purity by adding one of ethanol, ammonium sulfate, β alanine/glycine, a polymer (polyethyleneglycol), and a solution having a low degree of ionization to precipitate uniform fibrinogen at a relatively high yield, and additionally purifying the precipitated fibrinogen using the method such as ion exchange chromatography, affinity chromatography, and the like, but is not limited thereto.

In the present invention, the term "highly concentrated fibrinogen solution" means a fibrinogen solution obtained by concentrating the lowly concentrated fibrinogen solution using the ultra filtration method. A content of fibrinogen in the highly concentrated fibrinogen solution is not particularly limited as long as the content is higher than a predetermined concentration capable of being applied to the fibrin sealant product. However, the content may be higher than 40 mg/mL, preferably be higher than 70 mg/mL, and more preferably be 100 to 120 mg/mL.

Amino acid or the amino acid derivative capable of being added for ultra filtration of the lowly concentrated fibrinogen solution is not particularly limited, but preferably may be at least one selected from a group consisting of glycine, isoleucine, sodium L-glutamate, and L-arginine hydrochloride, and the salts capable of being added for the ultra filtration of the lowly concentrated fibrinogen solution is not particularly limited, but preferably may be sodium chloride or sodium citrate. This amino acid or amino acid derivative, and the salt prevent spontaneous clotting due to high concentration of fibrin during concentrating fibrin solution or during storing the highly concentrated fibrin solution after preparation, thereby serving to increase solubility and stability of the highly concentrated fibrinogen solution.

As amino acid or the amino acid derivative, and the salt contained in the highly or lowly concentrated fibrinogen solution according to the present invention, preferably, isoleucine may have a concentration of 10 to 70 mM, preferably, 40 to 50 mM, sodium L-glutamate may have a concentration of 10 to 50 mM, preferably, 20 to 30 mM, L-arginine hydrochloride may have a concentration of 5 to 30 mM, preferably, 10 to 20 mM, glycine may have a concentration of 50 to 200 mM, preferably, 100 to 150 mM, sodium citrate may have a concentration of 10 to 30 mM, and sodium chloride may have a concentration of 100 to 200 mM, and at least one material may be selected from amino acid or the amino acid derivative, and the salts having the concentration as described above and be added.

The highly or lowly concentrated fibrinogen solution according to the present invention may have a pH of 5 to 9, preferably 6 to 8, and more preferably 7 to 8.

As a membrane capable of being used for the ultra filtration in the present invention, any membrane may be used without limitation as long as the membrane may selectively filter fibrinogen. For example, a membrane may be made of a modified form of polyethersulfone or a cellulose material, but is not limited thereto. A cut-off value of the membrane used for the ultra filtration in order to prepare the highly concentrated fibrinogen solution in the present invention may be 50 to 300 kDa, and more preferably, be 80 to 150 KDa. A modified form of polyethersulfone or cellulose means a form in which a part of polyethersulfone or cellulose is substituted with substituent having a specific function, or the like. As a specific example of this membrane, Biomax or Ultracel (Millipore corp.), Centrasette (Pall Corp.), Sartocon (Satorius Corp.), or the like, may be used. The material and characteristics of the products was shown in the following Table 1.

TABLE 1

Membranes capable of being used in the ultra filtration and characteristics thereof

| Product name | Material | Type |
| --- | --- | --- |
| Biomax | Modified polyethersulfone | A screen: tight (Dilute protein or low viscosity solutions) C screen: coarse (Concentrated protein solution or high viscosity solution) V screen: loose (High viscosity solutions) |
| Ultracel | Regenerated Cellulose | A screen: tight (Dilute protein or low viscosity solutions) C screen: coarse (Concentrated protein solution or high viscosity solution) V screen: loose (High viscosity solutions) |
| Centrasette | Modified Polyethersulfone Regenerated cellulose (~50 kD) | Fine screen: dilute solution Medium Screen: Low-MediumViscosity Suspended Screen: HighViscosity |
| Sartocon | Polyethersulfone Hydrosart (stabilized cellulose) | — |

The ultra filtration of the lowly concentrated fibrinogen solution in order to obtain the highly concentrated fibrinogen solution may be performed at 10 to 37° C., and preferably, at 15 to 30° C., and the ultra filtration is not particularly limited, but may be performed within 2 hours, and preferably for 10 to 90 minutes.

Further, in the method for preparing a highly concentrated fibrinogen solution, the heat treating process may be performed before the ultra filtration in order to remove contamination risk by virus and increase safety.

At the time of the heat treatment, a concentration of protein (fibrinogen, factor XIII, or the like) contained in the solution, an ingredient and concentration of a stabilizer are important. That is, the protein may have a concentration of 1 to 5 mg/mL, preferably, 2 to 4 mg/mL, based on the entire solution, and as the stabilizer, sugars such as white sugar, or the like, may be preferable, but is not limited thereto. In addition, the heat treatment may be performed for 2 to 20 hours, preferably for 5 to 15 hours, and more preferably for 7 to 12 hours at 40 to 90° C., preferably at 50 to 70° C., and more preferably at 55 to 65° C. Further, in order to increase the stability of the heat treatment, an additional stabilizer such as glycine, or the like may be additionally added. In order to remove impurities generated after heat treatment and the stabilizer, a general separation and purification method such as anion chromatography, or the like may be used.

In another general aspect, there is provided a method for preparing the fibrin sealant ingredient 1 including adding factor XIII, or the like, in the method for preparing a highly concentrated fibrinogen solution, and the fibrin sealant ingredient 1 prepared by the method.

In the present invention, the term "fibrin sealant component 1", which is a solution that may be immediately used as the fibrin sealant product when the fibrin sealant component 2 configured of thrombin and calcium chloride is provided, means a solution in which fibrinogen, factor, and other necessary ingredients are contained.

The method for preparing a fibrin sealant component 1 according to the present invention further includes additionally adding factor XIII before or after the ultra filtration in the method for preparing a highly concentrated fibrinogen. That is, Factor XIII may be added to the lowly concentrated fibrinogen solution before the ultra filtration for preparing the highly concentrated fibrinogen, or be added to the highly concentrated fibrinogen solution after the ultra filtration.

It may be preferable in consideration of easiness of purification and virus inactivation that Factor XIII is added to the lowly concentrated fibrinogen solution before the ultra filtration to be used to prepare the fibrin sealant component 1, and in the case in which Factor XIII is added to the highly concentrated fibrinogen solution after the ultra filtration to be used to prepare the fibrin sealant component 1, the treatment such as the virus inactivation, or the like, may be performed in advance on added Factor XIII, or the like. In the case in which Factor XIII is added to the lowly concentrated fibrinogen solution before the ultra filtration to be subjected to the heat treatment process, which is the virus inactivation process, the protein in a preferable concentration of the protein at the time of the heat treatment is estimated to include fibrinogen and Factor XIII.

In the method for preparing a fibrin sealant component according to the present invention, a mixing ratio of Factor XIII to fibrinogen may be preferably 0.1 to 0.8 IU, preferably, 0.7 to 0.8 IU per 1 mg of fibrinogen in the highly concentrated fibrinogen solution. Factor XIII used in order to prepare the fibrin sealant component 1 in the present invention may be obtained from Fraction I precipitate obtained by ethanol precipitation from human blood plasma using generally known processes such as precipitation, heat denaturation, virus inactivation, anion chromatography, or the like.

In addition, the method for preparing a fibrin sealant component 1 according to the present invention may include adding at least one material selected from a group consisting of aprotinin, a detergent such as Tween series (Tween 20, Tween 80, or the like), and albumin to the highly concentrated fibrinogen solution containing Factor XIII after the ultra filtration.

Aprotinin may be contained in the fibrin sealant component 1 in a concentration of 100 to 5000 KIU/mL, preferably 200 to 3000 KIU/mL, albumin may be contained therein in a concentration of 2 to 50 mg/mL, preferably, 5 to 30 mg/mL, and the detergent such as Tween series (Tween 20, Tween 80, or the like) contained therein in a concentration of 0.01 to 0.05 weight %, preferably 0.02 to 0.04 weight %.

With the method for preparing a fibrin sealant component 1 according to the present invention, the fibrin sealant component 1 capable of being frozen in a liquid state may be provided without a freeze-drying process, or the like. In addition, in the fibrin sealant component 1 prepared by the method according to the present invention, a process of removing a virus is included in the preparing process, such that a problem caused by the virus derived from the blood does not occur and the fibrin sealant component 1 may be preserved for 2 to 8 months at 4 to 25° C. and be preserved more than 24 months at −18° C. or less. The final fibrin sealant component 1 according to the present invention may have a pH of 6.0 to 9.0, preferably, 7.0 to 8.0.

In another general aspect, there is provided a fibrin sealant product containing the fibrin sealant component 1 prepared according to the method described above and a method thereof.

The fibrin sealant product according to the present invention may be prepared by providing a fibrin sealant component 2 containing thrombin and calcium chloride filled in a separate container to the fibrin sealant component 1 prepared by the method described above, and the fibrin sealant product according to the present invention may be provided in a vial type in which the fibrin sealant component 1 and the fibrin sealant component 2 containing thrombin and calcium chloride are filled in separate vials, respectively, or a pre-filled type in which the fibrin sealant component 1 and the fibrin sealant component 2 are filled in separate syringes connected with each other to be immediately used (See FIG. 2), but is not limited thereto. In addition, those skilled in the art will appreciate that all of the types that are generally used in the art are included in the appended claims of the present inventions as long as they meet objects of the present invention.

The fibrin sealant component 2 containing thrombin and calcium chloride may contain 4 to 1200 IU/mL, preferably 400 to 600 IU/mL of thrombin and 20 to 60 mM, preferably 30 to 50 mM of calcium chloride.

In the fibrin sealant product according to the present invention, albumin may be additionally included in the fibrin sealant component 2 filled in the separate container. The fibrin sealant component 2 filled in the separate container contains 5 to 100 mg/mL, preferably 10 to 50 mg/mL of albumin.

More specifically, an example of the method for preparing a fibrin sealant product includes:

(1) precipitating human blood plasma using cryoprecipitation method;

(2) obtaining a lowly concentrated fibrinogen solution from the precipitated fractions;

(3) obtaining Factor XIII from a supernatant of the human blood plasma precipitated using the cryoprecipitation method;

(4) adding Factor XIII, amino acid, and/or a salt to the lowly concentrated fibrinogen solution and performing ultra filtration to obtain a fibrin sealant component 1 containing Factor XIII; and (5) providing a fibrin sealant component 2 filled in a separate container to the fibrin sealant component 1.

In the above method, those skilled in the art will appreciate that Step (2) and Step (3) may be performed in a changed sequence, and a heat treatment step may be additionally performed before performing the ultra filtration.

More specifically, another example of the method for preparing a fibrin sealant product includes:

(1') precipitating human blood plasma using cryoprecipitation method;

(2') obtaining a lowly concentrated fibrinogen solution from the precipitated fractions;

(3') obtaining Factor XIII from a supernatant of the human blood plasma precipitated using the cryoprecipitation method;

(4') adding amino acid, and/or a salt to the lowly concentrated fibrinogen solution and performing ultra filtration to obtain a highly concentrated fibrinogen solution;

(5') adding Factor AU, or the like, to the obtained highly concentrated fibrinogen solution to obtain a fibrin sealant component 1; and (6') providing the fibrin sealant component 1 and a fibrin sealant component 2 filled in a separate container.

In the above method, those skilled in the art will appreciate that Step (2) and Step (3) may be performed in a changed sequence, and a heat treatment step may be additionally performed before performing the ultra filtration.

Advantageous Effects

As set forth above, with the method for preparing a highly concentrated fibrinogen solution using the ultra filtration according to the present invention, the highly concentrated fibrinogen solution capable of being used to prepare the fibrin sealant may be economically, efficiently, and rapidly obtained without a freeze-drying process unlike the existing method.

In addition, since the fibrin sealant component 1 and the fibrin sealant product prepared using the highly concentrated fibrinogen solution prepared by the method described above may be provided in a liquid state to thereby be immediately used without reconstitution operation, the fibrin sealant component 1 and the fibrin sealant product may be convenient for clinical use, be preserved for a long time at room temperature, and be preserved for at least 24 months in the case of cryopreservation.

DESCRIPTION OF DRAWINGS

The above and other objects, features and advantages of the present invention will become apparent from the following description of preferred embodiments given in conjunction with the accompanying drawings, in which.

(a) commercially sold freeze-dried type product; and (b) liquid type fibrin sealant according to the present invention.

BEST MODE

Example 1: Preparation of a Highly Concentrated Fibrinogen Solution

A lowly concentrated fibrinogen solution and Factor XIII in the present invention were separated from human blood plasma and prepared. First, after cryoprecipitates were separated from the human blood plasma, a fibrinogen precipitate was prepared using cryoprecipitation method, virus inactivation method (using solvent/detergent (S/D) treatment method), anion chromatography method, glycine precipitation method (See FIG. 1).

Figure 1:
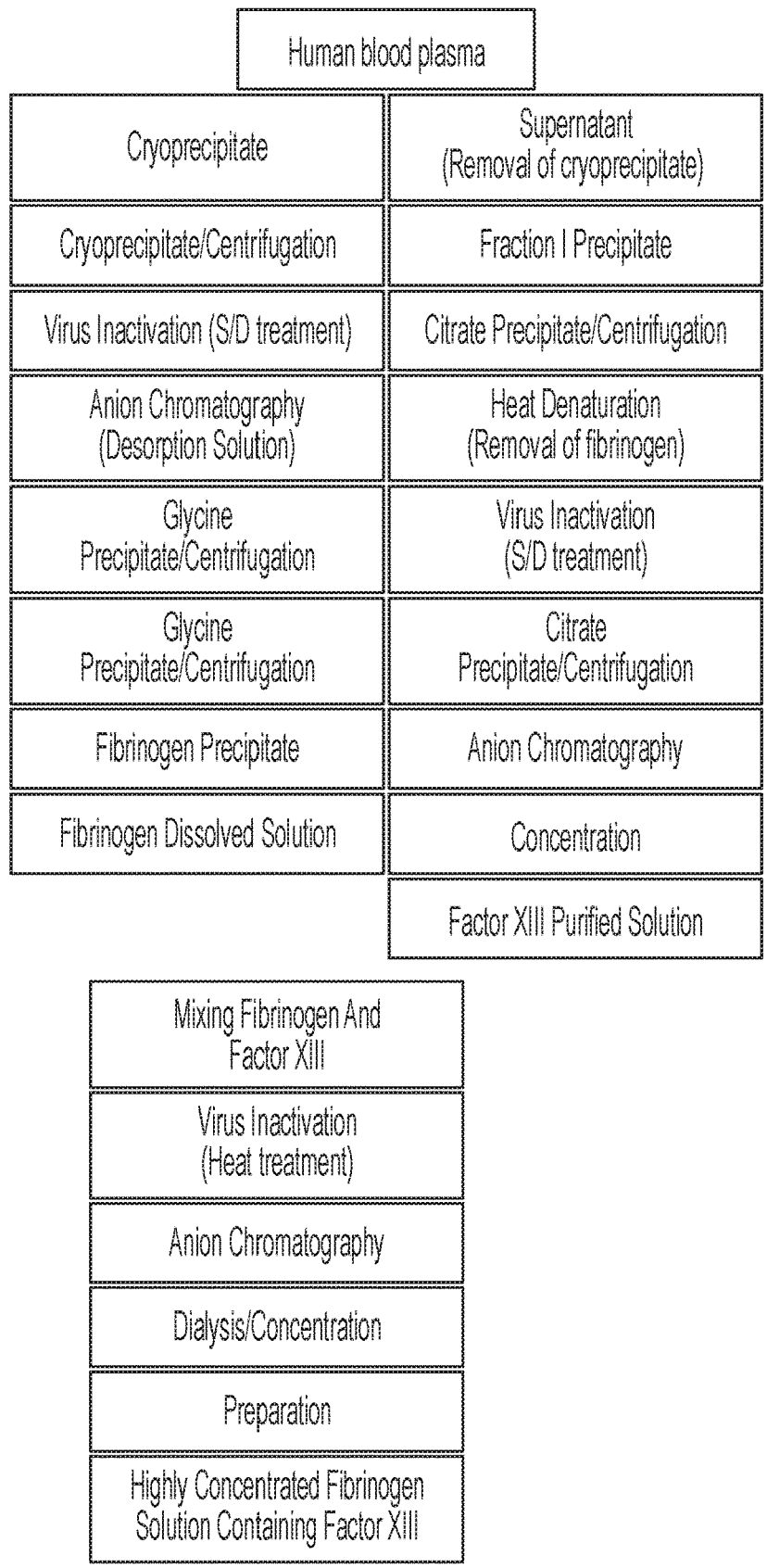
FIG. 1 is a view illustrating a method for preparing a highly concentrated fibrinogen solution containing Factor XIII.
Figure 2:
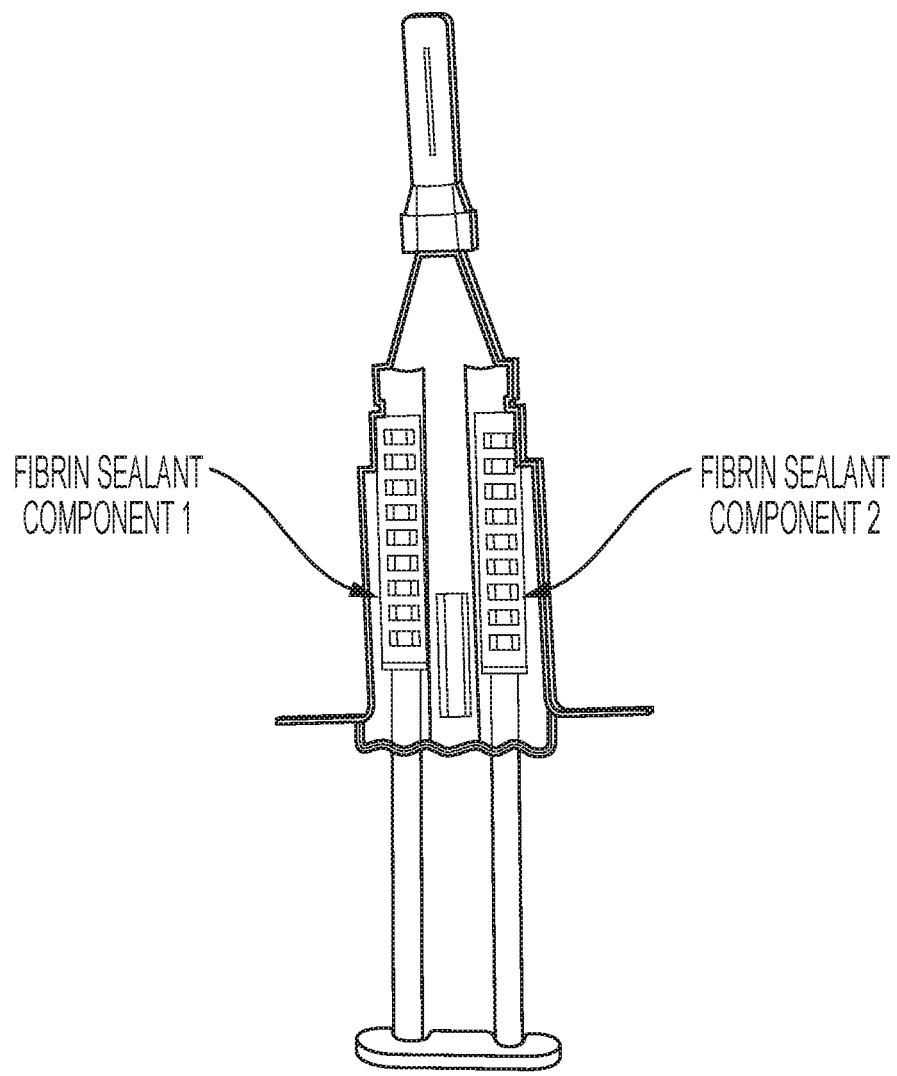
FIG. 2 is a view illustrating a pre-filled type product among fibrin sealant products according to the present invention.

After Factor XIII was prepared through a citrate precipitation process, the S/D treatment process, the anion chromatography process, and a concentration process from Fraction I precipitate obtained by ethanol precipitation after removing the cryoprecipitates from the human blood plasma, the fibrinogen precipitation was dissolved and mixed, and then heat treatment (for 10 hours, at 60° C.), which is the virus inactivation process, the anion chromatography process, a dialysis-concentration process were performed, such that a lowly concentrated fibrinogen solution having a protein concentration of about 40 mg/mL and containing Factor XIII (See FIG. 1).

The case in which amino acid was added to the lowly concentrated fibrinogen solution containing the Factor XIII and the case in which amino acid was not added thereto were divided, ultra filtrations were preformed, respectively.

In the case in which amino acid was added, the lowly concentrated fibrinogen solution containing the Factor XIII contained 50 mM of isoleucine, 30 mM of sodium L-glutamte, 20 mM of L-arginine hydrochloride, 150 mM of glycine, 20 mM of sodium citrate, 150 mM of sodium chloride, and 30 mg/ML of protein (Factor XIII and fibrinogen) at pH 7.5, and in the case in which amino acid was not added, the lowly concentrated fibrinogen solution containing the Factor XIII contained 20 mM of sodium citrate, 150 mM of sodium chloride, and 30 mg/mL of fibrinogen at pH 7.5. In all of the cases, the solution had a pH of 7.5.

The highly concentrated fibrinogen solution and the fibrin sealant component 1 were prepared by the ultra filtration. Here, Biomax™ (Millipore Corp.) was used as a membrane for the ultra filtration, and Pellicon 2 mini-cassettes (50 to 100 kDa, 0.1 m$^2$, A, C, and V type) were used.

The ultra filtration was performed in a state in which pressure at a side at which the solution enters the membrane of the ultra filtration was maintained to be 1 to 2 bar.

As a result, it was confirmed that in the case in which amino acids such as isoleucine, sodium L-glutamate, L-arginine hydrochloride, glycine, or the like, which are stabilizers, are contained, a highly concentrated fibrinogen solution having the maximum 140 mg/mL of Factor XIII is obtain within 2 hours, and even in the case in which fibrinogen is highly concentrated, spontaneous clotting does not occur, as shown in Table 2.

TABLE 2

Concentration efficiency of fibrinogen according to the ultra filtration membrane and addition of the stabilizer

| No. | Membrane (kDa) | Membrane (Type) | Addition of stabilizer | Maximum concentrated concentration (mg/mL) | characteristics observation | Concentrating time (H) |
|---|---|---|---|---|---|---|
| 1 | 50 | A | ○ | 60 | Good | 1 |
| 2 | 100 | A | X | 60 | Good | 1 |
| 3 | 50 | C | ○ | 100 | Good | 1.5 |
| 4 | 100 | C | X | 100 | Spontaneous clotting | 1.5 |
| 5 | 50 | V | ○ | 140 | Good | 2 |
| 6 | 100 | V | X | 140 | Spontaneous clotting | 2.5 |

Example 2: Stability of a Fibrin Sealant Component 1 According to Temperature Preservation Condition 10 mg/mL of albumin, 1000 KIU/mL of aprotinin, Tween were mixed with the highly concentrated fibrinogen solution prepared according to Example 1, such that the fibrin sealant component 1 was prepared.

The prepared fibrin sealant component 1 was sterilized by filtration using a 0.2 μm filter to be filled in a 1 mL syringe, such that the stability was confirmed according to preservation conditions. The fibrin sealant component 1 used in the present experiment contained 88 mg/mL of fibrinogen and 65 IU/mL of Factor XIII.

A period for which clotting protein of fibrinogen is reduced by 10% was measured as a preservable period, thereby estimating the stability.

As a result, it was observed that the fibrin sealant component 1 containing Factor XIII according to the present invention may be stably preserved for at least 24 months at −18° C. and be preserved up to 6 months at 25° C. (See Table 3).

TABLE 3

Stability of the fibrin sealant component 1 according to the preservation condition

| Preservation temperature | Fibrinogen content (mg/mL) | Factor XIII content (IU/mL) | Test cycle | Preservable period |
|---|---|---|---|---|
| −18° C. | 88 | 65 | 3 months | 24 months |
| 4° C. | 88 | 65 | 1 week | 2 months |
| 25° C. | 88 | 65 | 1 month | 6 months |
| 37° C. | 88 | 65 | 1 day | 3 days |

Example 3: Preparation of a Fibrin Sealant Product

A fibrin sealant component 2 containing thrombin and calcium chloride filled in a separate container was provided to the fibrin sealant component 1 prepared in Example 2 to prepare the fibrin sealant product, and finally, the two solutions are mixed with each other, such that the fibrin polymer is formed and may be used for medical purpose, or the like. In the fibrin sealant component 2 filled in the separate container, 500 IU/mL of thrombin and 40 mM of calcium chloride was contained, and 40 mg/mL of albumin may be additionally added.

Example 4: Electron Microscope Observation of the Fibrin Sealant

In order to compare and confirm physical properties when the fibrin sealant product prepared according to Example 3 forms the fibrin polymer and a freeze-dried type fibrin sealant (Greenplast 1 mL kit, Green Cross Corp.) commercially sold for treatment purpose forms the fibrin polymer, scanning electron microscope observation experiment was performed.

Figure 3A:
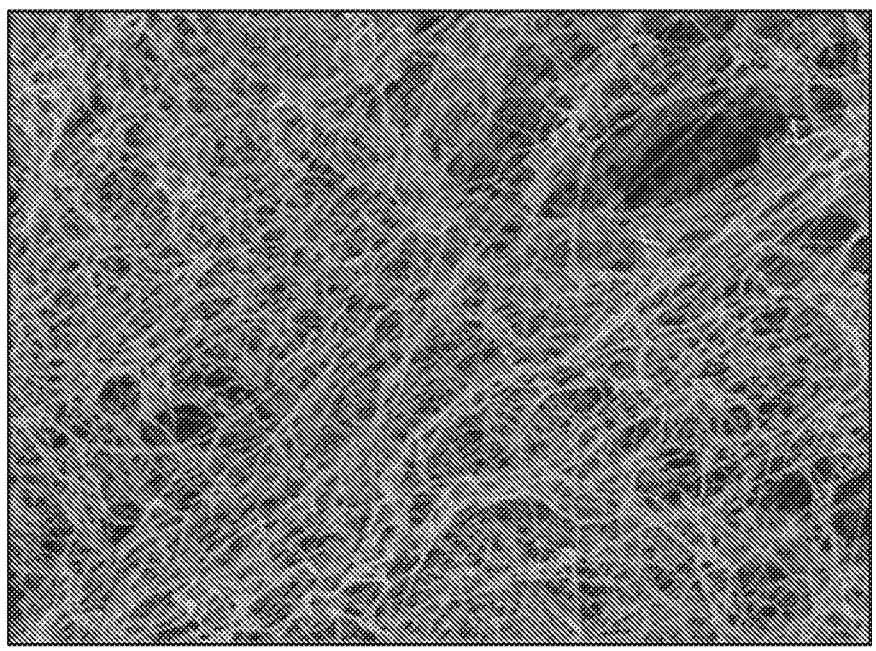
FIGS. 3A and 3B are photographs of a commercially sold freeze-dried type fibrin sealant product and a liquid type fibrin sealant product according to the present invention by an electron microscope.
Figure 3B:
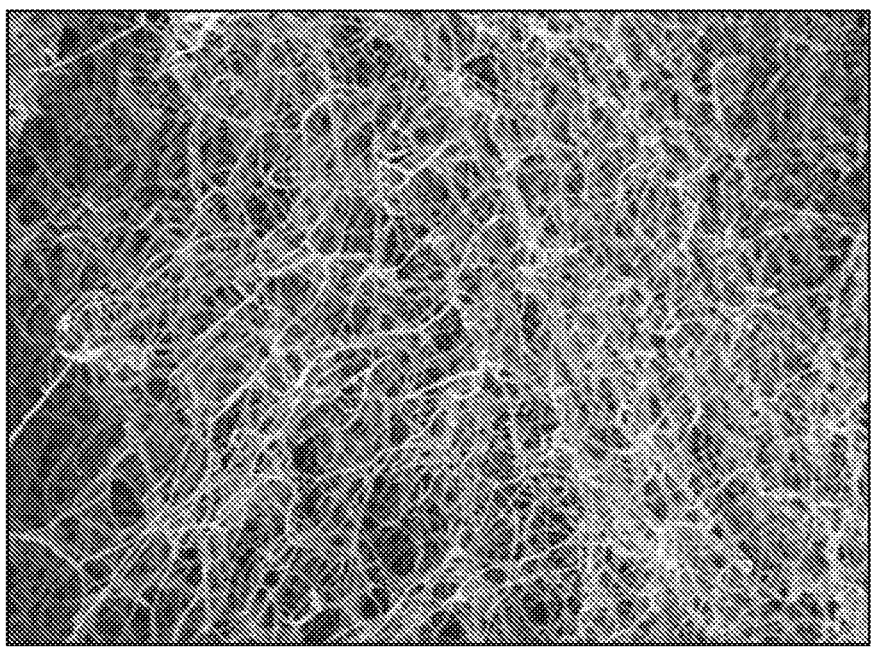

The scanning electron microscope used in the experiment was field emission scanning electron microscope (FESEM, equipment: Supra 55vp, Carl Zeiss, Germany). As a result, a fibrin clotting substance of the fibrin sealant product according to the present invention had a net shape in which fibrin was tangled like a skein of thread, similarly to that of the commercially sold freeze-dried fibrin sealant as shown in FIGS. 3A and 3B.

Example 5: Toxicity Test of a Fibrin Sealant

In order to test toxicity of the fibrin sealant product prepared according to Example 3, two kinds, that is, SD rats and rabbits were used. A low dose group (0.5 mL/kg) in which 5 times higher than the expected maximum clinical dose of the fibrin sealant product prepared according to the present invention was used and a high dose group (5 mL/kg) in which 50 times higher than the expected maximum clinical dose thereof was used were set, and toxicity reaction was estimated after single dose subcutaneous administration. After the test material was administrated to all of the female and male SD rats and rabbits, general symptom, weight, feed intake, hematologic examination, autopsy, histopathological examination were carried out for 14 days, and data was statistically treated.

As toxicity test results using the female and male rats and rabbits, all of the rats and the rabbits did not die, and an influence by the administration of the test material was not observed in weight, feed intake, and hematologic examination. In the general symptoms, indurations were observed at administration site of the test material administration group, and in the autopsy and histopathological examination, abnormalities were not observed in all of the organs and tissues except for foreign body reaction. Therefore, toxicological effect by the test material was not observed at doses up to 5 mL/kg in SD rats and rabbits, and it may be appreciated that a schematic lethal dose is higher than 5 mL/kg in both of female and male rats and rabbits.

The invention claimed is:

1. A method for preparing a fibrin sealant component 1 comprising:
   adding glycine 100-150 mM, isoleucine 40-50 mM, sodium L-glutamate 20-30 mM, L-arginine hydrochloride 10-20 mM, and a salt to a lowly concentrated fibrinogen solution;
   performing ultra filtration to obtain a highly concentrated fibrinogen solution;
   adding aprotinin, detergent, and albumin; and
   adding Factor XIII before or after performing the ultra filtration to obtain the fibrin sealant component 1;
   wherein the lowly concentrated fibrinogen solution has a fibrinogen content which is less than 40 mg/mL,
   wherein the highly concentrated fibrinogen solution has a fibrinogen content which is more than 70 mg/mL,
   wherein the ultra filtration is performed using a modified polyethersulfone membrane, said membrane having a cut-off value of 50 to 300 kDa at 15 to 30° C.,
   wherein the type of the membrane is C or V,
   wherein in the fibrin sealant component 1, the aprotinin is in a concentration of 100 to 5000 KIU/mL, the albumin is in a concentration of 5 to 30 mg/mL, and the detergent is in a concentration of 0.02 to 0.04 weight %,
   wherein the fibrin sealant component 1 is in a liquid state, which further comprises freezing the fibrin sealant component 1 for at least 24 months at −18° C. or less, and
   wherein Factor XIII is added so as to be 0.1 to 0.8 IU per 1 mg of fibrinogen in the highly concentrated fibrinogen solution.

2. The method of claim 1, wherein the adding Factor XIII is performed before performing the ultra filtration.

3. The method of claim 1, wherein the salt is sodium citrate or sodium chloride.

4. The method of claim 1, wherein the lowly or highly concentrated fibrinogen has a pH of 5 to 9.

5. A method for preparing a fibrin sealant product comprising:
   providing a fibrin sealant component 1, which comprises:
   adding glycine 100-150 mM, isoleucine 40-50 mM, sodium L-glutamate 20-30 mM, L-arginine hydrochloride 10-20 mM, and a salt to a lowly concentrated fibrinogen solution;
   performing ultra filtration to obtain a highly concentrated fibrinogen solution;
   adding aprotinin, detergent, and albumin; and
   adding Factor XIII before or after performing the ultra filtration to obtain the fibrin sealant component 1;
   wherein the lowly concentrated fibrinogen solution has a fibrinogen content which is less than 40 mg/mL,
   wherein the highly concentrated fibrinogen solution has a fibrinogen content which is more than 70 mg/mL,
   wherein the ultra filtration is performed using a modified polyethersulfone membrane, said membrane having a cut-off value of 50 to 300 kDa at 15 to 30° C.,
   wherein the type of the membrane is C or V,
   wherein in the fibrin sealant component 1, the aprotinin is in a concentration of 100 to 5000 KIU/mL, the albumin is in a concentration of 5 to 30 mg/mL, and the detergent is in a concentration of 0.02 to 0.04 weight %,
   wherein the fibrin sealant component 1 is in a liquid state, which further comprises freezing the fibrin sealant component 1 for at least 24 months at −18° C. or less, and
   wherein Factor XIII is added so as to be 0.1 to 0.8 IU per 1 mg of fibrinogen in the highly concentrated fibrinogen solution,
   providing a fibrin sealant component 2 containing thrombin and calcium chloride filled in a separate container.

6. The method of claim 5, wherein the fibrin sealant product is a vial type in which the fibrin sealant component 1 and fibrin sealant component 2 are filled in separate vials, respectively, or a pre-filled type in which the fibrin sealant component 1 and the fibrin sealant component 2 are filled in separate syringes connected with each other to thereby be immediately used.

7. The method of claim 5, wherein in the fibrin sealant component 2, thrombin has a concentration of 4 to 1200 IU/mL, and calcium chloride has a concentration of 20 to 60 mM.

8. The method of claim 5, wherein the fibrin sealant component 2 additionally contains albumin in a concentration of 10 to 50 mg/mL.

* * * * *